(12) United States Patent
McLachlan

(10) Patent No.: US 6,570,060 B2
(45) Date of Patent: May 27, 2003

(54) MILK LACKING β-CASEIN A[1]

(76) Inventor: Corran Norman Stuart McLachlan, 29 Summer St, North Shore (NZ)

(*) Notice: Subject to any disclaimer, the term of this patent is extended or adjusted under 35 U.S.C. 154(b) by 21 days.

(21) Appl. No.: 09/906,807

(22) Filed: Jul. 18, 2001

(65) Prior Publication Data

US 2002/0166129 A1 Nov. 7, 2002

Related U.S. Application Data

(63) Continuation-in-part of application No. 09/500,801, filed on Feb. 10, 2000, now abandoned, which is a continuation of application No. 08/645,219, filed on May 13, 1996, now abandoned.

(30) Foreign Application Priority Data

May 16, 1995 (NZ) ............................................... 272133

(51) Int. Cl.[7] .......................... A01K 67/00; C12Q 1/68; A61K 35/20; A23C 1/00
(52) U.S. Cl. .............................. 800/8; 435/6; 424/535; 426/491; 426/580
(58) Field of Search ............................ 800/15; 435/6; 424/535; 426/491, 580

(56) References Cited

U.S. PATENT DOCUMENTS 5,106,618 A    4/1992 Beck et al. .............. 424/157.1

FOREIGN PATENT DOCUMENTS

| EP | 0 631 731 | 1/1995 |
| WO | WO 95/10192 | 4/1995 |
| WO | WO 96/14577 | 5/1996 |

OTHER PUBLICATIONS

Ng–Kwai–Hang et al. Association Between Genetic Polymorphism of Milk Production Traits during Three Lactations. Journal of Diary Science. 1990, vol. 73, pp. 3414–3420.*

K.F. Ng Kwai Hang, "Genetic Polymorphism of Milk Proteins: Influence on Milk Yield and Composition", Bulletin of the IDF, 304, 1987, pp. 6–7.

Ng–Kwai–Hang et al., "Association Between Genetic Polymerphism of Milk Proteins and Production Traits During Three Lactations", Journal of Dairy Science, vol. 73, No. 12, 1990, pp. 3414–3420.

Van Eenennaam et al., "Milk Protein Polymorphisms in California Dairy Cattle" Journal of Dairy Science, vol. 374, No. 5, 19991, pp. 1730–1742.

Fehily et al., "Diet and Incident Ishaemic Heart Disease: The Caerphilly Study", British Journal of Nutrition, 1993, vol. 69, pp. 303–314.

McLean et al., "Effect of Milk Protein Genetic Variants on Milk Yield and Composition", Journal of Dairy Research, vol. 51, 1984, pp. 531–546.

Aleandri et al., "The Effects of Milk Protein Polymorphisms on Milk Components and Cheese–Producing Ability" Journal of Dairy Science, vol. 73, No. 2, 1990, pp. 241–255.

Wong et al., Fundamentals of Dairy Chemistry, Third Edition, Chapter 2, Van Nostrand Reinhold, New York, 1988.

Bovenhuis et al., "Estimation of Milk Protein Gene Frequencies in Crossbred Cattle by Maximum Likelihood Method", Journal of Dairy Science, 74:2728, 1991, pp. 2549–2559.

Gonyon et al., "Associations of Bovine Blood and Milk Polymorphisms with Lactation Traits: Holsteins", Journal of Dairy Science, vol. 70, No. 12, 1987, pp. 2585–2598.

Biss et al., "Some Unique Biologic Characteristics of the Masai of East Africa", The New England Journal of Medicine, vol. 284, No. 13, Apr. 1, 1997, pp. 694–699.

Shaper, "Cardiovascular Studies in the Samburu Tribe of Northern Kenya", Am. Heart J., Apr. 1962, pp. 437–442.

R. J. Wall, "Transgenic Livestock: Progress and Prospects for the Future", Theriogenelogy, vol. 45, 1996, pp. 57–68.

L. Houdebine, "Production of Pharmaceutical Proteins from Transgenic Animals", Journal of Biotechnology, pp. 269–287.

M.Baringa et al., "Knockout Mice: Round Two" Science, vol. 265, Jul. 1994, pp. 26–27.

Y. Kawamoto et al., "A Population Genetic Study on Yaks Cattle and Their Hybrids in Nepal Using Milk Portein Variations", Animal Science Technology, vol. 63, No. 6, 1992, pp. 563575.

E. Jakob et al. "Implications of Genetic Polymorphism of Milk Proteins OFN Production and Processing of Milk", Bulletin of the IDF, 304, 1987, pp. 2–3, 6–8.

Ng–Kwai–Hang et al., "Genetic Polymorphism of Milk Proteins, in Advanced Diary Chemistry: 1 Proteins", P.F.Fox, ed. Eisevier, London, 1994.

J.R. Campbell et al., "The Science of Providing Milk for Man", McGraw–Hill Book Co., 1975, pp. 3, 31, 131–132, 252–253, 352, 545 and 616–617.

* cited by examiner

Primary Examiner—Deborah Crouch
(74) Attorney, Agent, or Firm—Young & Thompson

(57) ABSTRACT

A milk which is free of β-casein A[1] protein in the prevention or treatment of coronary heart disease is disclosed. In addition, a process for the testing of DNA from cells obtained from lactating bovines for the presence of DNA encoding certain β-casein proteins, selecting the bovines on the basis of the testing, and then milking those bovines to produce milk free of β-casein A[1] for use in the prevention or treatment of coronary heart disease is disclosed.

22 Claims, 8 Drawing Sheets

A¹ and A² Amplicons for the ACRS Genotyping Method

A² Amplicon          5'  GAGTAAGAGGAGGGATGTTTTGTGGGAGGCT CT t agggatgggccc......
A² template 3' ...ccaaactcattctcctccctacaaaacaccctccgacaatccctacccgggttccc......

A¹ Amplicon          5'  GAGTAAGAGGAGGGATGTTTTGTGGGAGGCT CT t agtgatgggccc......
A¹ template 3' ...cccaaactcattctcctccctacaaaacaccctccgacaataccctacccgggttccc......

FIG. 5

Electrophoresis Results for the ACRS Genotyping Method

FIG. 7

Gene Fragment Amplified in the Primer Extension Genotyping Method

5'ACTGGATTATGGACTCAAAGATTTGTTTCCTTCTTTCCAGGATGAACTCCGGAT
AAATCCACCCTTTGCCCAGACACAGTCTCTAGTCTATCCCTTCCCTGGGCCCAT
CC[A/C]TAACAGCCTCCCACAAAACATCCCTCCTCTTACTCAAACCCTGTGGTG
GTGCCGCCTTTCCTTCAGCCTGAAGTAATGGGAGTCCAAGTGAAGGAGGCTA
TGGCTCCTAAGCA[A/C]AAAGAAATGCCCTTCCCTAAATATCCAGTTGAGCCCTTT
ACTGAAAG[C/G]CAGAGCCTGACTCTCACTGATGTTGAAAATCTGCACCTT-3'

Mass Spectrometry Profile Results for the Primer Extension Genotyping Method

MILK LACKING β-CASEIN A¹

This is a continuation-in-part of application Ser. No. 09/500,801, filed on Feb. 10, 2000, abandoned, which is continuation of application Ser. No. 08/645,219, abandoned.

FIELD OF THE INVENTION

This invention relates to the use of milk which is free of the β-casein $A^1$ protein in the prevention or treatment of coronary heart disease. The invention also relates to the testing of DNA from cells obtained from lactating bovines for the presence of DNA encoding certain β-casein proteins, selecting the bovines on the basis of the testing, and then milking those bovines to produce milk free of β-casein $A^1$ for use in the prevention or treatment of coronary heart disease.

BACKGROUND OF THE INVENTION

Coronary heart disease is a major cause of death, particularly in countries where the populations are well-nourished, such as in the western world. Many factors are implicated as risk factors for this disease including obesity, smoking, genetic predisposition, diet, hypertension, and cholesterol.

Dairy products, especially milk, are a major contributor to the dietary intake of humans, again particularly in western world populations. Milk contains numerous components of nutritional and health benefit. Calcium is one example. However, milk is also a significant source of dietary fat. It is widely accepted that saturated fats found in milk are a risk factor for coronary heart disease. However, the inventor has discovered an additional risk factor present in some bovine milk unrelated to the fat content. What is entirely surprising is the source of the risk. The source is not dependent on the fat content of milk. Instead, it is a milk protein, β-casein, which is linked to coronary heart disease.

A number of variants of milk proteins have been identified. Initially, three variants of β-casein were discovered (Aschaffenburg, 1961) and were denoted A, B and C. It was later found that the A variant could be resolved into $A^1$, $A^2$ and $A^3$ by gel electrophoresis (Peterson et. al. 1966). The β-casein variants now known are $A^1$, $A^2$, $A^3$, B, C, D, E and F, with $A^1$ and $A^2$ being present in milk in the highest proportions. It is anticipated that other variants may be identified in the future.

The inventor has determined that it is the milk protein β-casein $A^1$ which represents the risk factor in bovine milk that is linked to coronary heart disease, or at least is the principal risk factor. This determination on the part of the inventor forms the basis of the present invention.

There is no relationship between the fat content of milk and β-casein genotype in cows. Therefore, selecting cattle on the basis of milk fat content will not identify which bovines produce the novel risk factor, namely the specific β-casein variant, in their milk.

There is no significant difference in the fat content of milk produced by cows which are homozygous for the β-casein $A^1$ allele (i.e. $A^1A^1$) and cows which are homozygous for the β-casein $A^2$ allele (i.e. $A^2A^2$). This is apparent from studies reported in the literature.

Ng-Kwai-Hang has carried out several studies. One study (Ng-Kwai-Hang et. al., 1990) suggested that milk containing β-casein $A^1$ rather than β-casein $A^2$ may have a slightly higher fat content. However, these differences were very small. The differences between milk from $A^1$ homozygous cows and milk from $A^2$ homozygous cows were 0.05% (for the first lactation period), 0.07% (for the second lactation period), and 0.04% (for the third lactation period).

In another study, Ng-Kwai-Hang (in an abstract cited by Jakob et. al;, 1990) found the opposite effect (i.e. the $A^1A^1$ product had a lower fat content than the $A^2A^2$ product). Thus, the 1995 Ng-Kwai-Hang abstract directly contradicts the Ng-Kwai-Hang, et. al., 1990 study.

McLean et. al., 1984 (McLean) also reported that there was no significant difference in the fat content of milk from cows of $A^1A^1$ and $A^2A^2$ genotypes (mean±standard error: 45.8±2.6 g/l for milk of $A^1A^1$ cows and 48.6±1.9 g/l for milk of $A^2A^2$ cows).

Aleandri et. al., 1990 (Aleandri), shows in Table 5 that the least squares estimates of the effects of different genotypes and their standard errors on fat percentage in milk are 0.12±0.09 for $A^1A^1$ cows and 0.07±0.09 for $A^2A^2$ cows. Taking into account the standard error for the test, Aleandri indicates that the effects of $A^1A^1$ and $A^2A^2$ genotypes on milk fat content are equivalent.

Bovenhuis et. al., 1992 (Bovenhuis), highlights that there are statistical problems associated with the way in which the genotype effects on fat percentages in milk are studied and documented. It is stated that the ordinary least squares estimates may be biased. Bovenhuis points out that the analysis of the effect of a particular genotype on various characteristics of milk is complex in nature and may, among other things, be affected by other genes which may be linked to the gene under study. Bovenhuis attempts to take into account the above variables and to overcome statistical problems by using an animal model method.

Table 3 of Bovenhuis indicates that, for a statistical model in which each milk protein gene is analysed separately and the $A^1A^1$ cows designated as being the standard (i.e. given a value of 0% fat attributable to the genotype), the $A^2A^2$ genotype was estimated not to contribute (i.e. 0%) to the fat content of the milk of the animals harbouring that genotype when compared to the $A^1A^1$ genotype. The standard error of the test is recorded as 0.02%. Where a statistical model was used in which all milk protein genes were analysed simultaneously (Table 4 of Bovenhuis) and the $A^1A^1$ genotype was again designated as being the standard (at 0% fat content attributable to the $A^1A^1$ genotype), the $A^2A^2$ genotype was estimated to contribute to the fat content of the milk at −0.01% when compared with the $A^1A^1$ genotype. In this study a standard error of 0.02 was designated. Taking into account the standard error of the tests these results indicate that the $A^2A^2$ genotype contributes to the fat content of milk in an equivalent manner to the genotype $A^1A^1$.

Gonyon et. al., 1987 reached the same conclusion as Bovenhuis.

The level of individual components in milk is influenced by both the genotype and the environment. That is, the variation between animals in milk output or milk composition is due to both genotypic and phenotypic factors. For example, Bassette et. al., 1988 (Bassette) indicates that the composition of bovine milk may be influenced by a number of environmental factors and conditions other than genetic factors. Environmental factors may impact on milk production and the constituents contained within the milk (including fat content). For example, changes in milk composition occur due to:

the stage of lactation (e.g., the fat content of colostrum is often higher; the concentration of fat changes over a period of many weeks as the cow goes through lactation);

the age of the cow and the number of previous lactations;

the nutrition of the cow including the type and composition of feed consumed by the cow;

seasonal variations;

the environmental temperature at which the cows are held;

variations due to the milking procedure (e.g., the fat content of milk tends to increase during the milking process which means that for an incomplete milking the fat content would generally be lower than normal and for a complete milking the fat content will be higher than normal); and milking at different times of the day.

It is therefore apparent from the studies in this field that a person skilled in the relevant area of technology would not find a link between the fat content of milk and the β-casein genotype of the milk-producing bovines from which that milk is produced.

Thus, the inventor has for the first time identified the milk protein β-casein $A^1$ as a risk factor linked to coronary heart disease in its own right. It is therefore an object of this invention to provide a method of using milk substantially free of β-casein $A^1$ to prevent or treat coronary heart disease or to minimise the risk of developing coronary heart disease, or to at least provide a useful alternative. It is also an object of the invention to provide a method of producing milk substantially free of β-casein $A^1$ suitable for use in the prevention or treatment of coronary heart disease or the minimisation of the risk of developing coronary heart disease, or to at least provide a useful alternative.

SUMMARY OF THE INVENTION

In one aspect of the invention there is provided a method of preventing or treating coronary heart disease in a human which includes the step of at least reducing the intake in that human of β-casein $A^1$.

Preferably the reduction is effected by the human ingesting milk obtained from one or more lactating bovines, or a product processed from that milk, where the milk or product ingested is substantially free of β-casein $A^1$.

Preferably the milk is substantially free of βcasein $A^1$ but contains any one or more of β-caseins $A^2$, $A^3$, B. C, D and E.

More preferably the milk is substantially free of β-caseins $A^1$, B and C but contains any one or more of β-caseins $A^2$, $A^3$, D and E. Most preferably the milk is substantially free of β-caseins $A^1$, B and C and contains only β-casein $A^2$.

In a second aspect of the invention there is provided a method of producing milk suitable for use in the treatment or prevention of coronary heart disease from one or more lactating bovines which milk is substantially free of β-casein $A^1$ but which contains any one or more of β-caseins $A^2$, $A^3$, B, C, D and E, the method including the steps of:

(i) testing DNA or RNA from cells containing DNA or RNA obtained from the one or more lactating bovines for the presence of DNA or RNA encoding β-casein $A^1$;

(ii) selecting bovines which do not have any DNA or RNA encoding β-casein $A^1$; and (iii) milking the selected bovines.

In another aspect of the invention there is provided a method of producing milk suitable for use in the treatment or prevention of coronary heart disease from one or more lactating bovines which milk is substantially free of β-casein $A^1$, B and C but which contains any one or more of β-caseins $A^2$, $A^3$, D and E, the method including the steps of:

(i) testing DNA or RNA from cells containing DNA or RNA obtained from the one or more lactating bovines for the presence of DNA or RNA encoding any one or more of β-caseins $A^1$, B and C;

(ii) selecting bovines which do not have any DNA or RNA encoding any one or more of β-caseins $A^1$, B and C; and (iii) milking the selected bovines In another aspect of the invention there is provided a method of producing milk suitable for use in the treatment or prevention of coronary heart disease from one or more lactating bovines which milk is substantially free of β-casein $A^1$ but which contains β-casein $A^2$, the method including the steps of:

(i) testing DNA or RNA from cells containing DNA or RNA obtained from the one or more lactating bovines for the presence of DNA or RNA encoding β-casein $A^2$;

(ii) selecting bovines which are homozygous for DNA or RNA encoding β-casein $A^2$; and (iii) milking the selected bovines.

In another aspect of the invention there is provided a method of producing milk suitable for use in the treatment or prevention of coronary heart disease from one or more lactating bovines which milk is substantially free of β-casein $A^1$ but which contains any one or more of β-caseins $A^2$, $A^3$, D and E, the method including the steps of:

(i) testing DNA or RNA from cells containing DNA or RNA obtained from the one or more lactating bovines for the presence of DNA or RNA encoding any one or more of β-caseins $A^2$, $A^3$, D and E;

(ii) selecting bovines which have DNA or RNA encoding only for any one or more of βcaseins $A^2$, $A^3$, D and E; and (iii) milking the selected bovines.

In another aspect of the invention there is a method of producing milk suitable for use in the treatment or prevention of coronary heart disease from one or more lactating bovines which milk is substantially free of β-casein $A^1$ but which contains β-casein $A^2$, the method including the steps of:

(i) testing DNA or RNA from cells containing DNA or RNA obtained from the one or more lactating bovines for the presence of DNA or RNA encoding β-casein $A^1$ and DNA or RNA encoding β-casein $A^2$;

(ii) separating bovines which are homozygous for DNA or RNA encoding β-casein $A^2$ from bovines which either have DNA or RNA encoding β-casein $A^1$ or which have DNA or RNA encoding both 3-casein $A^1$ and β-casein $A^2$; and (iii) milking the bovines which are homozygous for DNA or RNA encoding β-casein $A^2$.

In another aspect of the invention there is provided a method of producing milk suitable for use in the treatment or prevention of coronary heart disease from one or more lactating bovines which milk is substantially free of β-caseins $A^1$, B and C but which contains any one or more of β-caseins $A^2$, $A^3$, D and E, the method including the steps of:

(i) testing DNA or RNA from cells containing DNA or RNA obtained from the one or more lactating bovines for the presence of DNA or RNA encoding any one or more of β-caseins $A^1$, B and C and DNA or RNA encoding any one or more of β-caseins $A^2$, $A^3$, D and E.

(ii) separating bovines which have any DNA or RNA encoding any one or more of β-caseins $A^1$, B and C from bovines which have DNA or RNA encoding only for any one or more of β-caseins $A^2$, $A^3$, D and E; and (iii) milking the bovines which have DNA or RNA encoding only for any one or more of β-caseins A², A³, D and E.

Preferably the one or more lactating bovines of any aspect of this invention are *Bos taurus* bovines More preferably the milk produced according to any aspect of this invention is substantially free of β-casein A¹ and the β-casein contained in the milk comprises greater than 95% by weight β-casein A².

More preferably the milk produced according to any aspect of this invention is substantially free of β-casein A¹ and the β-casein contained in the milk comprises approximately 100% by weight β-casein A².

BRIEF DESCRIPTION OF THE DRAWINGS

FIG. 5 shows the A¹ and A² amplicons for the ACRS genotyping method (SEQ ID NOS 1, 10, 13 and SEQ ID NOS 1, 11, 41, respectively, in order of appearance).

FIG. 7 shows the gene fragment amplified in the Primer Extension genotyping method (SEQ ID NO: 12).

DETAILED DESCRIPTION OF THE INVENTION

Figure 1:
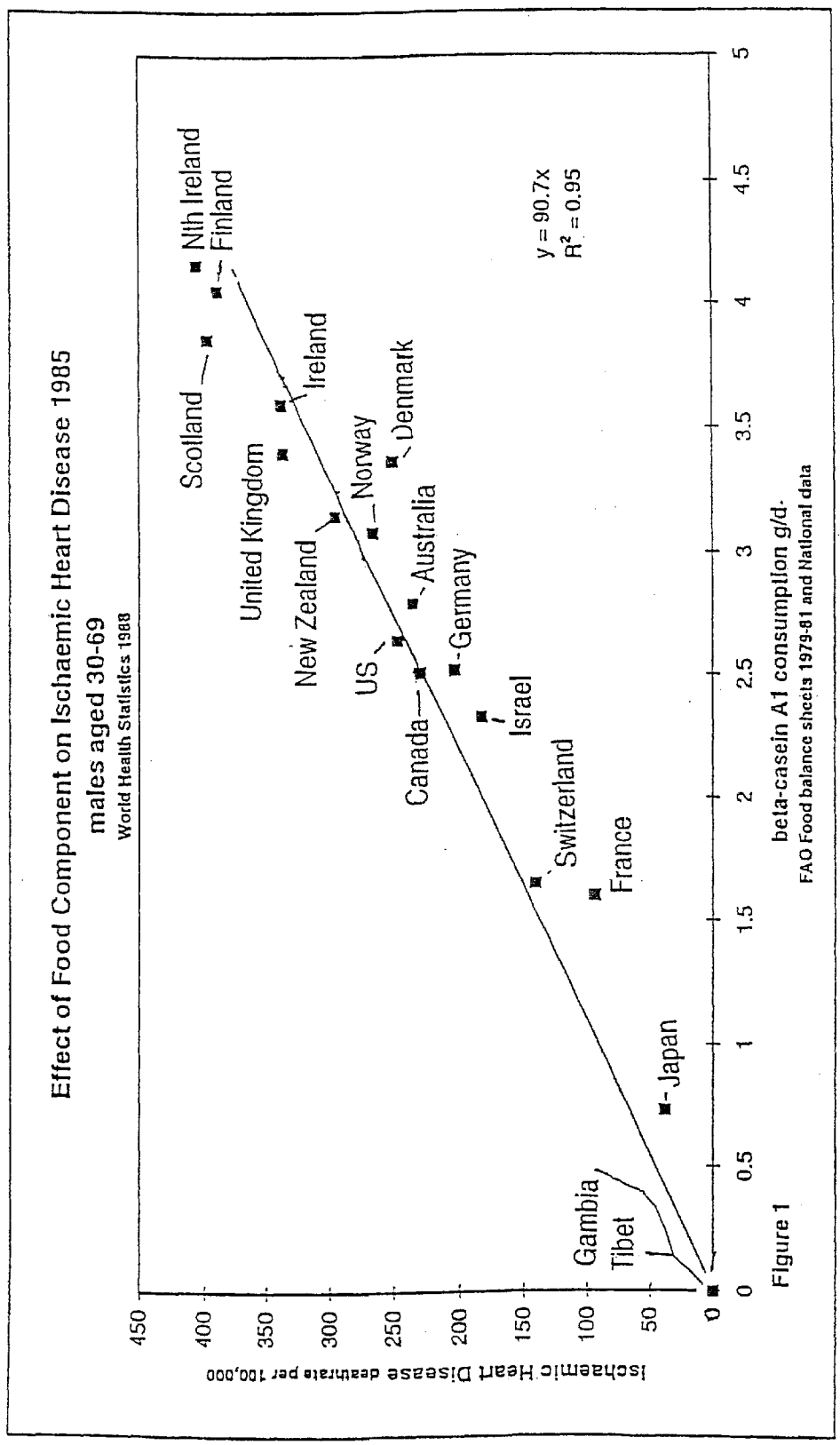
FIG. 1 is a graph showing the regression relationship between the death rate from Ischaemic Heart Disease (all ages per 100,000 of population for the year 1985) and the estimated average daily intake of β-casein A¹ per head of population (based on country by country dietary information and data on the genotype of the dairy cows in their national herds), over a number of countries

This invention is applicable to milk, and all products processed from that milk, which milk is substantially free of β-casein A¹.

As used herein, the term "treatment" in relation to coronary heart disease means at least a reduction in the risk of a coronary heart disease event occurring in a human. The terms "treat" and "treating" have equivalent meanings.

Coronary heart disease means any disease or disorder relating to the coronary heart system and includes atherosclerosis and ischaemic heart disease.

The term "*Bos taurus*" refers to any cow whose pedigree from its three prior generations is 50% or more of *Bos taurus* origin.

The term "β-casein A¹ allele" is a term used with reference to one of the variant forms of the β-casein gene. Expression of the A¹ allele results in the production of the β-casein A¹ protein. Where reference is made to the presence of the β-casein A¹ allele in an individual or population, it encompasses both homozygous and heterozygous genotypes with respect to that allele. Similarly, where reference is made to the presence of β-casein A¹, it encompasses phenotypes resulting from either a homozygous or heterozygous state with respect to the β-casein A¹ allele.

An example of an animal which is heterozygous for β-casein is a β-casein A¹A² bovine. Some animals are homozygous, for example bovines that are A¹A¹ for β-casein and those that are A²A² for β-casein. A β-casein A²A² bovine is capable of producing only the β-casein A² protein.

Genetic variation within a species is due at least in part to differences in the DNA sequence. While there are relatively few such differences in relation to the number of DNA bases or the size of the genome, they can have a major impact as is evident in the genetic heterogeneity of the human and bovine populations. For example, in bovines, a mutation in the DNA sequence coding for the β-casein protein at nucleotide position 200 has resulted in the replacement of a cytidine base with an adenine base. Thus, the triplet codon affected by this change codes for histidine (CAT) rather than for proline (CCT) at amino acid position 67 of the protein. Thus, the histidine at position 67 results in the cow producing β-casein A¹ while the proline results in the cow producing β-casein A² (Note: the preceding discussion assumes that the ancestral bovid expressed β-casein A² and that there are no other DNA variations at other positions on the DNA sequence).

The term "substantially" as used in the expression "substantially free of β-casein A¹" reflects that it cannot be said with 100% certainty that a sample of milk is absolutely free of β-casein A¹. On rare occasions, and despite all efforts to ensure that a herd is β-casein A¹ free, an animal capable of producing β-casein A¹ in its milk could present itself in the herd because of a genetic mutation or because of human error. Herds are formed by the genotype testing of animals and then selecting the desired individuals. All such testing is subject to human error. The phrase "substantially free of β-casein A¹" is therefore intended to account for this. Without the word "substantially", the phrase would be unduly limiting.

The products processed from milk that form part of this invention are derived from a source of bulk milk (i.e. milk from more than one animal) and include, but are not limited to:

(a) bulk milk
(b) bulk milk used to make cheese whether or not the milk has been pasteurised, sterilised or otherwise treated to reduce the the population of microbes prior to cheese making,
(c) milk powders,
(d) milk solids,
(e) caseins, caseinates, and casein hydrolysates,
(f) pasteurised, sterilised, preserved milks including microfiltered milks, UHT milks,
(g) low fat milks,
(h) modified or enhanced milks,
(i) ice-cream or other frozen dairy based confections,
(j) fermented milk products such as yoghurt or quark,
(k) cheeses including full fat, partial de-fatted and fat-free processed cheeses,
(l) milk whey,
(m) food products enriched through the addition of milk products such as soups,
(n) milk from which potentially allergenic molecules have been removed, (o) confections such as chocolate,
(p) carbonated milk products, including those with added phosphate and/or citrate,
(q) infant formulations which may contain full, partially de-fatted or nonfat milk together with a number of additional supplements,
(r) liquid or powdered drink mixtures, and
(s) buttermilk and buttermilk powder.

It has been reported that certain human population groups exhibit a relatively low incidence of coronary heart disease and certain other diseases, notwithstanding the fact that they consume considerable quantities of milk and milk proteins. These people include the Tibetans, rural Gambians, and the Masai and Samburu people of Kenya. The inventor has identified the fact that a major difference between these population groups and other similar population groups is that the milk consumed by the above people is derived from *Bos indicus* bovines (e.g. the Zebu breed) and from the Yak (*Bos grunniens*). Such milk does not contain β-casein $A^1$.

In addition, a comparative study in Denmark of the causes of morbidity in the Greenland Eskimo population and the predominant Danes, shows very large relative differences that are suggestive of differences in life-style risk factors. One notable difference is that the Danes are large consumers of dairy products whereas the Eskimos are not. The differences in morbidity are illustrated in Table 1 below.

TABLE 1

Age-adjusted differences in morbidity from chronic diseases between Greenland Eskimos and Danes

|  | Eskimos/Danes |
|---|---|
| Acute myocardial infarction | 1/10 |
| Stroke | 2/1 |
| Psoriasis | 1/20 |
| Diabetes | Rare |
| Bronchial asthma | 1/25 |
| Malignant disorders | 1/1 |
| Thyrotoxicosis | rare |
| Multiple sclerosis | 0 |
| Polyarthritis chronica | Low |

Acta Med. Scand., 208: 401–406, (1980)

A further comparison has been carried out using data from the states of the former West Germany. In this case, the coronary heart disease death rates have been found to correlate strongly with the relative regional average consumption of β-casein $A^1$ (Table 2). In this instance, the composition of the individual state dairy herds remained virtually constant from the 1950's through to the 1980's.

The data show a remarkable relationship between the relative incidence of Ischaemic Heart Disease and the relative average consumption of β-casein $A^1$ across the 8 states. This is in marked contrast to the relatively poor relationships between the incidence of Ischaemic Heart Disease and the recognised listed dietary risk factors.

TABLE 2

A comparison of the relative nutritional risk factors for coronary heart disease and the incidence of Ischaemic Heart Disease (IHD) in the states of the former Federal Republic of Germany (Schleswig-Holstein = 1.00)

|  | Relative intake of dietary component | | | | | | Relative |
|---|---|---|---|---|---|---|---|
|  | Saturated Fat | Cholesterol | Alcohol | Carbohydrates | Energy | β-$A^1$ casein | incidence of IHD |
| Schleswig Holstein | 1.00 | 1.00 | 1.00 | 1.00 | 1.00 | 1.00 | 1.00 |
| Niedersachsen | 0.97 | 0.96 | 1.00 | 0.98 | 0.99 | 0.92 | 0.88 |
| Nordrhein Westfalen | 0.99 | 1.02 | 0.99 | 1.00 | 1.02 | 0.97 | 1.00 |
| Hessen | 0.95 | 0.96 | 0.98 | 0.98 | 0.98 | 0.75 | 0.74 |
| Rheinland-Pfalz | 0.95 | 0.99 | 1.00 | 1.02 | 1.0 | 0.87 | 0.78 |
| Saarland | 0.94 | 0.93 | 0.98 | 1.01 | 0.98 | 0.90 | 0.88 |
| Baden Wurttenburg | 0.93 | 1.02 | 1.02 | 1.05 | 1.03 | 0.50 | 0.72 |
| Bayern | 0.96 | 0.99 | 1.22 | 1.06 | 1.02 | 0.50 | 0.74 |

A regression relationship between Ischaemic Heart Disease and fat intake was conducted and was shown to be not significant ($p<0.0684$, $r^2=0.20$). However, the regression between Ischaemic Heart Disease and the intake of β-casein $A^1$ was highly significant ($p<0.0001$, $r^2=0.71$). The regression relationships are:

$$IHD = 1.56\ (\pm 0.79)\ \text{Fat Intake} + 86.7\ (\pm 74.9)$$

$$IHD = 81.7\ (\pm 13.5)\ \beta\text{-Casein } A^1 - 5.4\ (\pm 40.4)$$

The multiple regression relationship was then generated. In this case, the inclusion of both fat intake and β-casein $A^1$ intake did not improve the relationship over that with β-casein $A^1$ alone. The regresion relationship is:

$$IHD = 78.3\ (\pm 15.6)\ \beta\text{-Casein } A^1 + 0.259\ (\pm 0.557)\ \text{Fat} - 19.2\ (\pm 51.0)$$

The analyses of the relationships between various dietary factors and Ischaemic Heart Disease outlined in this document indicate the potential importance of the β-casein variant as a risk factor for heart disease. The difference between the two casein variants is only one amino acid. This suggests that the products of proteolysis of these variants may be linked to the identified risk factor. Some indication of the number, and the major product fragments into which they are split by proteolytic action of a variety of enzymes, is illustrated for the β-caseins in Table 3.

TABLE 3

The β-casein family of proteins

| Former Nomenclature | Recommended Nomenclature | Source of Fragment |
|---|---|---|
| β-casein $A^1$ | β-CN $A^1$-5P | — |
| β-casein $A^2$ | β-CN $A^2$-5P | — |
| β-casein $A^3$ | β-CN $A^3$-5P | — |
| β-casein B | β-CN B-5P | — |
| β-casein C | β-CN C-4P | — |
| β-casein D | β-CN D-4P | — |
| β-casein E | β-CN E-5P | — |
| $\gamma_1$-casein $A^1$ | β-CN $A^1$-1P(f29–209) | β-CN $A^1$-5P |
| $\gamma_1$-casein $A^2$ | β-CN $A^2$-1P(f29–209) | β-CN $A^2$-5P |
| $\gamma_1$-casein $A^3$ | β-CN $A^3$-1P(f29–209) | β-CN $A^3$-5P |
| $\gamma_1$-casein B | β-CN B-1P(f29–209) | β-CN B-5P |
| $\gamma_2$-casein $A^2$ | β-CN $A^2$ (f106–209) | β-CN $A^1$-5P or β-CN $A^2$-5P |
| $\gamma_2$-casein $A^3$ | β-CN $A^3$ (f106–209) | β-CN $A^3$-5P |
| $\gamma_2$-casein B | β-CN B (f106–209) | β-CN B-5P |
| $\gamma_3$-casein A | β-CN A (f108–209) | β-CN $A^1$-5P, β-CN $A^2$-5P or β-CN $A^3$-5P |
| $\gamma_3$-casein B | β-CN B (f108–209) | β-CN B |

In addition there are a number of protease peptone components.
Elgel, W.N., Nomenclature of Proteins of Cow's Milk: Fifth Revision J. Dairy Sci., 67: 1599–1631, (1984)

Bovine milk is an important source of proteins and other nutrients required by humans. A high proportion of the common domestic cattle breeds, such as the Holstein, express the β-casein $A^1$ allele. For example, it is estimated that in the late 1980s more than 70% of the Californian dairy herd carried the $A^1$ allele. As noted previously, the β-casein $A^1$ variant is of particular interest and therefore, considering its contribution to milk consumed by the human population in many parts of the world, the proteolysis products of β-casein $A^1$ are of particular interest.

Figure 2:
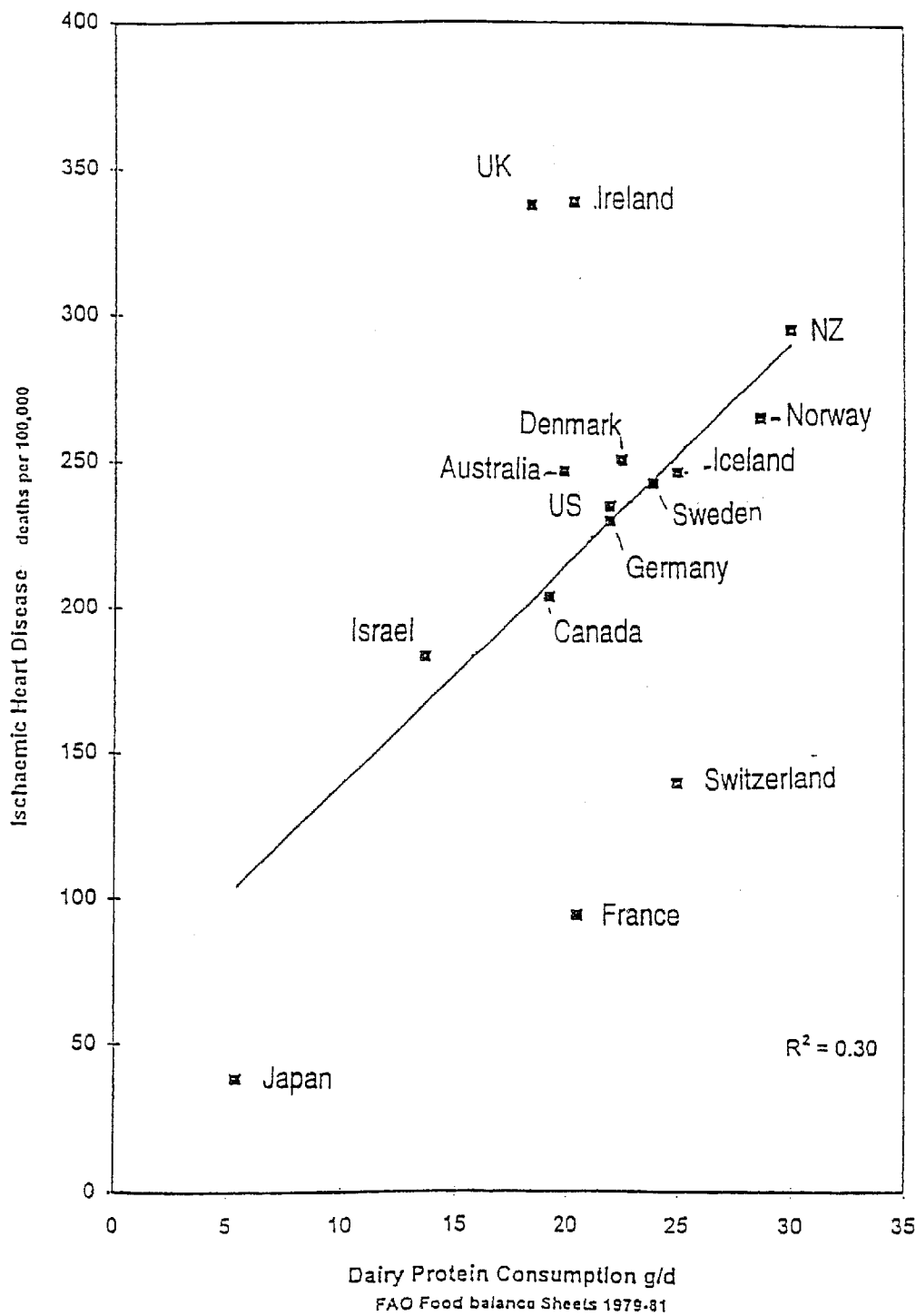
FIG. 2 is a graph showing the regression relationship between the death rate from Ischaemic Heart Disease (per 100,000 males aged 30–69 for the year 1985) and the estimated average daily intake of dairy protein per head of population over a number of countries.
Figure 3:
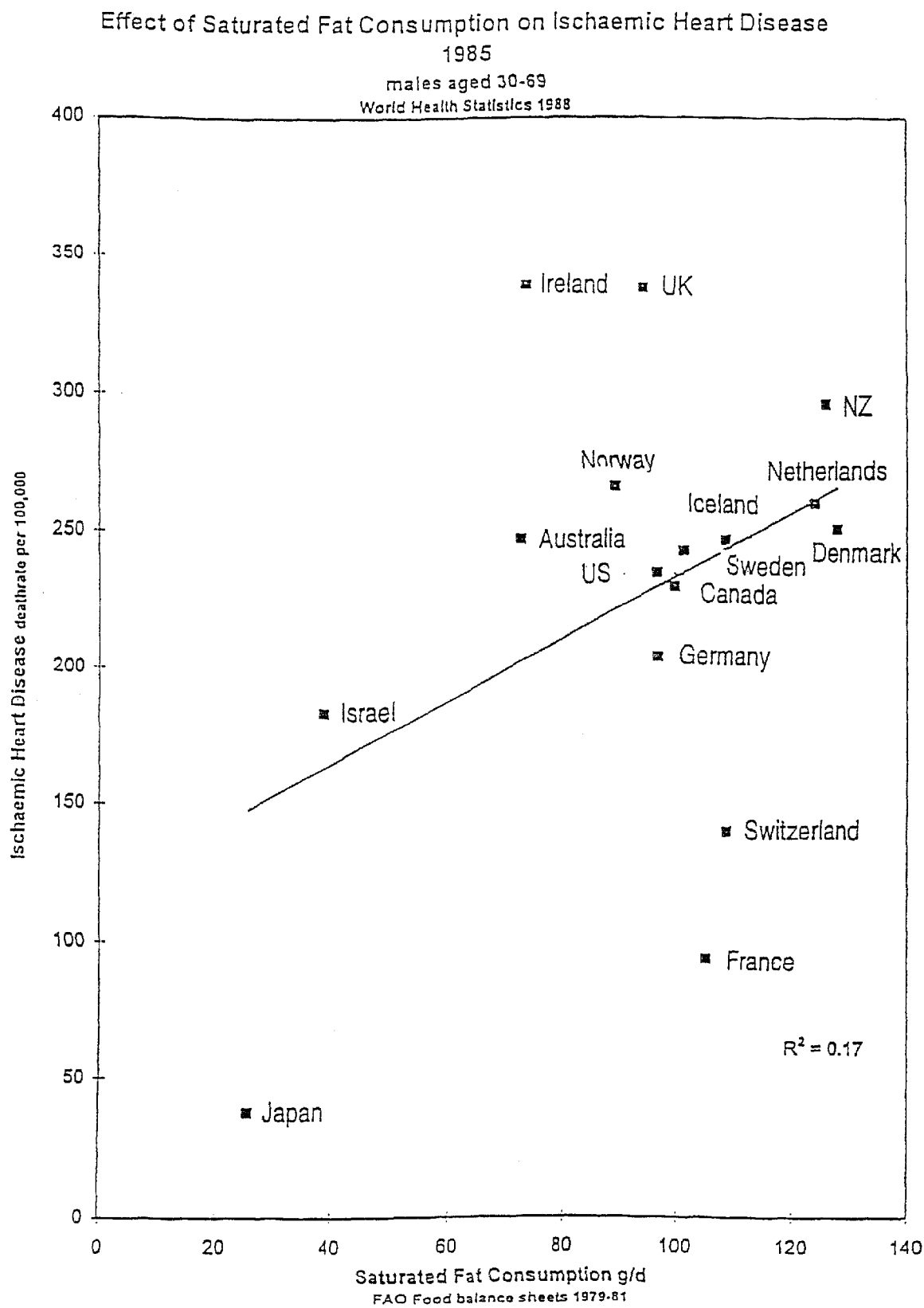
FIG. 3 is a graph showing the regression relationship between the death rate from Ischaemic Heart Disease (per 100,000 males aged 30–69 for the year 1985) and the estimated average daily intake of saturated fat over a number of countries.
Figure 4:
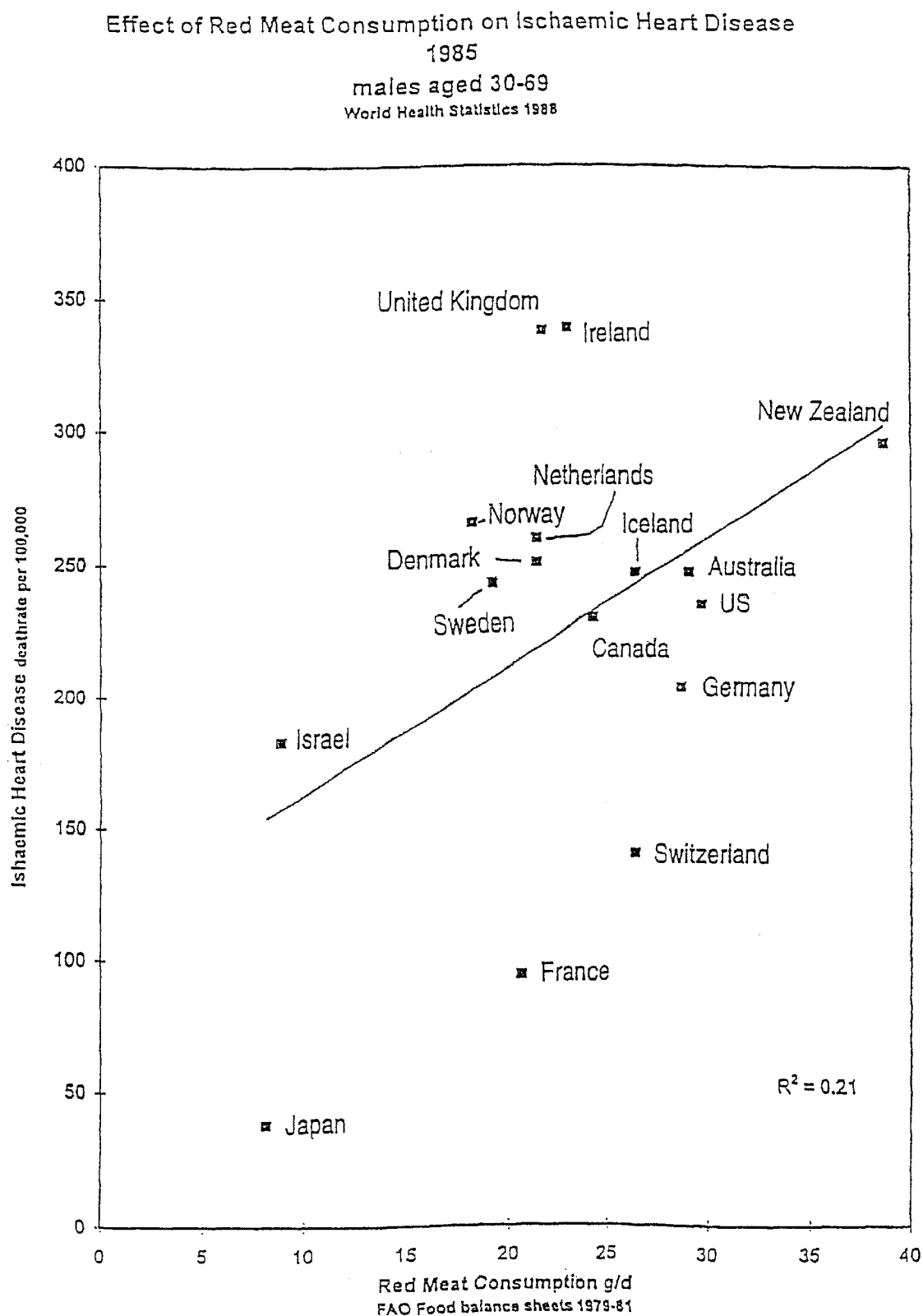
FIG. 4 is a graph showing the regression relationship between the death rate from Ischaemic Heart Disease (per 100,000 males aged 30–69 for the year 1985) and the estimated average daily intake of red meat over a number of countries.

In the graph shown in FIG. 1, the incidence of Ischaemic Heart Disease is plotted against the estimated average consumption of β-casein $A^1$ (and its derived proteolysis products). FIG. 1 shows a very strong correlation between the consumption of β-casein $A^1$ and death rate from Ischaemic Heart Disease. In contrast, the correlation with the consumption of dairy protein (FIG. 2) is much lower: Neither saturated fat consumption (FIG. 3) nor the consumption of red meat (FIG. 4) show the strong correlation which the inventor has identified in relation to the consumption of β-casein $A^1$, both between countries and within countries.

The single amino acid difference between the two predominant β-casein variants has highlighted the potential role of a difference in the proteolysis products from different β-casein variants as potential risk factors for coronary heart disease. Therefore, the potential impact of pasteurisation is of interest, as prolonged heating is a factor that is known to influence proteolysis. In particular, this relates to the more severe forms of heat treatment that were used in the early years of pasteurisation (e.g. Holder pasteurisation which heats milk to 63° C. and holds it for 20–30 minutes). Hence the impact of the introduction of Holder pasteurisation on the death rate from coronary heart disease is of interest. The inventor has examined the available data and the results of the analyses are presented in Table 4.

The analyses reveal a very marked and sudden increase in the death rate from coronary heart disease in the four years after the introduction of Holder pasteurisation. Such data would suggest the presence of a novel risk factor associated with pasteurisation. It is the inventor's contention that this risk factor may be associated with a derivative of beta-casein $A^1$ (for example, a proteolysis product).

TABLE 4

Comparison of the death rates due to coronary heart disease before and after the introduction of Holder Pasteurisation in different parts of the UK

| Population group | Holder intro. year | Angina pectoris (AP1) mort. per mill. | | | | Cerebral embolism and thrombosis (CET) | | | |
|---|---|---|---|---|---|---|---|---|---|
| | | AP1 | AP2 | AP3 | Δ % | CET1 | CEL2 | CET3 | Δ % |
| U.K. | | | | | | | | | |
| Edinburgy | 1923 | 1925 | 67 | 92 | 37[a] | 1924 | 174 | 236 | 36 |
| Glasgow | 1924 | 1924 | 56 | 91 | 62[a] | 1924 | 77 | 101 | 31 |
| Dundee | 1924 | 1925 | 42 | 64 | 52[a] | 1925 | 162 | 188 | 16 |
| Aberdeen | 1926 | 1926 | 91 | 135 | 48[a] | 1927 | 121 | 227 | 88 |
| Lanarkshire (excluding Glasglow) | 1935 | 1937 | 188 | 375 | 99[b] | 1938 | 153 | 193 | 26 |
| | 1947 | 1948 | 685 | 1185 | 73 | 1948 | 298 | 518 | 74 |
| | 1952 | 1954 | 1185 | 1523 | 29 | 1954 | 518 | 680 | 31 |
| Country of Sutherland | 1954 | 1954 | 963 | 1710 | 78 | 1954 | 610 | 823 | 35 |
| Country of Bute | 1956 | 1956 | 1610 | 2848 | 78 | 1956 | 955 | 1398 | 46 |

TABLE 4-continued

Comparison of the death rates due to coronary heart disease before and
after the introduction of Holder Pasteurisation in different parts of the UK

| Population group | Holder intro. year | Angina pectoris (AP1) mort. per mill. | | | | Cerebral embolism and thrombosis (CET) | | | |
|---|---|---|---|---|---|---|---|---|---|
| | | AP1 | AP2 | AP3 | Δ % | CET1 | CEL2 | CET3 | Δ % |
| London Admin. | 1925 | 1925 | 31 | 112 | 261[c] | 1926 | 90 | 120 | 33 |
| County Average increase | | | | | 82 | | | | 42 |
| Norway Oslo | 1922 | 1922 | 3 | 43 | 1333.3[d] | not available | | | |

Columns AP1 and CET1 denote the year of commencement of the sudden rise in the appropriate mortality.
Columns AP2 and CET2 denote the appropriate average mortality for the 4 years immediately preceeding the year of introduction.
Columns AP3 and CET3 denote the appropriate average mortality for the 4 years immediately succeeding the introduction of pasteurisation.
Δ % represents average increase.
[a]Possibly low because deaths ascribed to "coronary thrombosis" were not included in International List No. 89 in Scotland until 1931.
[b]Possibly high as deaths ascribed to "coronary thrombosis" were included in International List No, 94.
[c]Possibly high because after 1927 all deaths ascribed to "coronary thrombosis" were included (unlike those in Scotland) in International List No. 89.
[d]Mortality ascribed to the following classification groups: angina pectoris, infarctus cordis, sclerosis art. coron. Cordis.

It is possible, however, that a specific fragment or fragments of β-casein A¹ affect the body's immune system as a result of their immunosuppressant properties. By reducing or substantially eliminating the presence of β-casein A¹ in the diet of an individual, it is believed that its immune response may be enhanced, or immunosuppression reduced, thereby improving the general well-being of the individual. It is believed that some individuals may be particularly susceptible to the presence of β-casein A¹, and it may be possible to develop a test for such susceptible individuals, and to recommend that they reduce or eliminate the consumption of milk or other dairy products containing β-casein A¹.

In humans, low density lipoprotein (LDL) oxidation is considered to be a primary step in the evolution of artherosclerotic damage (Steinberg et. al., 1989). Analysis of protein oxidation products isolated from atherosclerotic lesions implicates the tyrosyl radical (a reactive nitrogen species) and hypochlorous acid in LDL oxidation (Heinecke et. al., 1999). In addition, it has been found (Torreilles and Guerin, 1995) that peptides from bovine casein hydrolysates could promote peroxidase-dependent oxidation of human LDLs. The reaction is independent of free metal ions but requires casein-derived peptides with tyrosyl end residues. This implies that the tyrosyl ending peptide is a diffusable catalyst that conveys oxidising potential from the active site of the heme enzyme to LDL lipids. Casomorphin-7 is a potential source of a tyrosyl radical. It is produced from β-casein A¹ but not β-casein A² (Jinsmaa et. al., 1999).

Recognising that dairy products free from β-casein A¹ are desirable, it is preferable to ensure that the animal from which the product is derived has been tested for the presence of the β-casein A¹ allele. Subsequent separation of the bovines into separate herds and/or selective breeding programmes (selecting for β-casein A¹ negative animals) can be carried out to eliminate the presence of the β-casein A¹ from the herd. It will be recognised that such testing may be carried out in a number of ways without departing from the scope of the present invention.

Any known method for the genotyping of bovines may be used. Such methods can be specific for DNA or RNA encoding either β-casein A¹ or β-casein A². However, general methods which do not specifically test for DNA or RNA encoding β-casein A¹, but additionally test for DNA or RNA encoding other β-caseins, may also be used to form a herd of bovines which do not produce β-casein A¹ or produce only β-casein A² in their milk.

For the avoidance of any doubt, any reference to DNA in the methodology of this invention is intended to include cDNA (which is DNA derived from RNA).

For example, it is known that β-casein A¹ has histidine at position 67 of the protein whereas β-casein A² has proline at the same position. This is due to the presence of an adenine nucleotide at position 200 of the β-casein DNA. This produces the triplet codon that specifies histidine (CAT) rather than proline (CCT). A test which identifies the codon that will specify histidine at position 67 of the β-casein protein can therefore be used to exclude bovines which produce β-casein A¹ in their milk.

Similarly, a test which identifies the codon that will specify proline at position 67 of the β-casein protein can therefore be used to select bovines which produce β-casein A² (or β-caseins A³, D or E) in their milk. While a test for animals that are homozygous for the presence of CCT (that codes for proline) at codon 67 of an animal's β-casein gene does not unequivically show whether or not the animal is homozygous for the β-casein A² allele, the test can show that an animal does not possess any of the alleles for β-casein A¹, B and C. Such a test does not need to be any more specific because culling animals negative for the test will mean the elimination of β-casein A¹ producing animals from the herd.

It is also known that β-caseins B and C, in addition to β-casein A¹, have histidine at position 67. Also, β-caseins A³, D and E, in addition to β-casein A², have proline at position 67. Therefore, a test which distinguishes between the codons that specify proline and histidine at position 67 will also distinguish between β-caseins A¹, B and C on the one hand and β-caseins A², A³, D and E on the other hand.

For example, while a test for the presence of CAT (histidine) or absence of CCT (proline) in one or other or both of an animal's alleles at codon 67 of its β-casein gene does not unequivocally show whether or not the animal contains the β-casein A¹ allele, the test can show that an animal may contain one or more of the alleles for β-casein A¹, B and C. Such a test does not need to be any more specific because culling animals positive for the test (i.e. absence of the proline codon in at least one allele) will mean the elimination of β-casein A¹ producing animals from the herd.

A DNA or RNA test which gives positive identification for animals homozygous for CCT (proline) at codon 67 can therefore be used to ascertain whether a particular bovine does not possess a β-casein A¹ allele, whether homozygous or heterozygous. Thus, bovines which do possess the CCT (proline) at codon 67 at one or both alleles can therefore be culled from a herd to give a herd which is free of the β-casein A¹ allele. Milk obtained from that herd therefore cannot contain β-casein A¹.

Where it is known that the genetic makeup of the herd is such that the only possible alleles possessed by the individuals are for β-caseins A¹ and A², the culling from the herd of those bovines positive for histidine at position 67 gives a herd where each individual is homozygous for the β-casein A² allele. Such a herd will produce milk possessing only β-casein A².

The determination of whether the genotype at codon 67 of the β-casein gene is CCT (proline) or CAT (histidine) can be made by many different methods that are available and which could be used to assay for this single nucleotide polymorphism (SNP). The methods include DNA sequencing, SSCP (single stranded conformation polymorphism), allele specific amplification, and assays designed using proprietary chemistries such as Taqman™ (PE Biosystems), Invader™ (Third Wave Technologies), SnapShot™ (PE Biosystems), Pyrosequencing™ (Pyrosequencing AB), Sniper™ (Pharmacia), and DNA chips (hybridisation or primer extension chips).

The preferred method should have the ability to function well with rapidly extracted impure DNA. High test throughput (>1000 of samples per day) at low cost is desirable. Since the preferred objective is to identify bovines that are homozygous for the β-casein A² allele, the unequivocal positive identification of animals homozygous for CCT at codon 67 is preferred, rather than simply the absence of a result in a test for the alternative CAT codon.

Two examples of practical methods for the large scale genotyping of bovines are:
- A manual ACRS (amplification created restriction site) method which can be conducted easily in any molecular genetics laboratory and requires no specialist equipment or devices. The method can be easily scaled up to analyse hundreds of samples per day.
- A highly automated method such as the Sequenom™ primer extension and mass spectrometry system which is capable of analysing thousands of samples per day The aim of the ACRS method is to create an amplicon in which only one allele of an SNP will form a restriction site. The restriction site is created by site directed mutagenesis in the amplification step.

A Dde1 restriction site can be created when the nucleotides CT are present at nucleotide 200 and 201 (positions 2 and 3 of codon 67) of the β-casein gene. This would positively identify the presence of the CCT (proline) codon.

In Example 1 below, the 3' section of the Casein Dde2 primer has a mismatch at its penultimate nucleotide (FIG. 5). This is important as it creates a Dde1 restriction site in the A² amplicon only (shown in italics in FIG. 5). In FIG. 5, codon 67 in each template is in bold lowercase. The template is reversed to present the primer in the usual 5'-3' orientation. The mismatch base is underlined.

Variations of the test could include modification of the sequence of the 5' end of the Casein Dde2 primer or 5' extension of the Casein Dde2 primer with a nucleotide sequence homologous to the β-casein template or 5' extension of the Casein Dde2 primer with nucleotides which are not homologous to the β-casein sequence. The second primer for the ACRS is less critical and many compatible primers could be used. The primer known as Casein4 5'-CCTTCTTTCCAGGATGAACTCCAGG-3' (SEQ ID NO: 2) has been found to be the most effective.

PCR amplification with this pair of primers produces a 121 base pair fragment in all β-casein alleles. However, the definitive diagnostic step is that only alleles with CT at positions 200 and 201 (i.e. specifying amino acid 67 of the β-casein) can be cut with the restriction enzyme Dde1. This produces distinctive 86- and 35-base pair fragments.

The first step of the primer extension method is PCR amplification of the region of the β-casein gene containing codon 67. In Example 2 below, a 319 bp fragment (shown in FIG. 7), was amplified. In FIG. 7, the primer regions are shown underlined. Alternate bases of the SNP are shown bracketed.

The post PCR product is cleaned with a SAP reaction to remove unincorporated dNTPs. An extension primer complementary to the bold itallicised sequence is added to the cleaned product along with an extension mixture containing ddA, ddC, ddT and dG. The following size extension products are obtained:

|             | Name      | Sequence (5'-3')         | SEQ ID NO: | Mass (Da) |
|-------------|-----------|--------------------------|------------|-----------|
| Primer      | AGR-RMA6  | GTTTTGTGGGAGGCTGTTA      | 3          | 5920.90   |
| Contaminant | (Pause)   | GTTTTGTGGGAGGCTGTTAG     | 4          | 6250.10   |
| Analyte     | A         | GTTTTGTGGGAGGCTGTTAT     | 5          | 6209.10   |
| Analyte     | C         | GTTTTGTGGGAGGCTGTTAGGGA  | 6          | 7205.70   |

If codon 67 of β-casein is CAT, a 20 bp, 6209.10 Dalton product is obtained, whereas if the sequence is CCT, a 23 bp, 7205.70 Dalton product is obtained. These products can be clearly distinguished and separated from possible contaminants by MALDI-TOF mass spectrometry.

The results of the genotype testing obtained from either method are then used to select bovines positively identified as having CCT (proline) at position 67 at both alleles. Such bovines cannot produce β-casein A¹ in their milk. The selected bovines are kept in a separate herd and are milked separately. Ideally the milk from that separate herd is kept separate from other milk which may contain β-casein A¹.

The selected bovines may be uniquely identified (e.g. alternatives include ear-tagging with a unique tag, or use of an electronic tag or use of a specific tag that identifies the bovine as being free of the β-casein A¹ allele or branding for future identification). The selected bovines are milked to give milk free of β-casein A¹. Preferably, the milk is phenotype tested to confirm that the milk is substantially free of β-casein A¹.

A bulk quantity of milk from the selected bovines may then be processed into one or more milk products, such as fresh milk, cheeses, yoghurts, milk powders etc.

Finally, it will be appreciated that various other alterations and modifications may be made to the foregoing without departing from the spirit or scope of this invention.

EXAMPLES

Example 1

ACRS Method

At least 10 hairs were pulled from the end of the tail switch of a cow so that the hook-shaped follicles were retained on the end of the removed hairs. This was achieved easily by pulling the tail hairs upward while holding the rest of the switch down. If the tail has been docked, longer hairs from the end of the docked tail or other locations on the body may be substituted. Tail hairs are preferred.

Five hair follicles from one cow were cut into a sterile 1.5 ml microfuge tube. Solution A (200 μl) was added to the tube and the tube placed in a boiling water bath for 15 minutes. The tube was removed and Solution B (200 μl) added followed by mixing.

Solution A (200 mM NaOH)

Solution B (100 mM Tris-HCl, pH 8.5 with an extra 200 mM HCl)—prepared by combining 1 M Tris-HCl, pH 8.5 (10 ml) with conc. HCl (1.67 ml) and making up to 100 ml with distilled water.

Crude DNA extract (1.5 μl) from hair follicles (prepared as above) or DNA (20–50 ng) (prepared by another method) was transferred to a well of a 96-well PCR plate. PCR cocktail (20 μl) was added to the well. The well was overlayed with mineral oil and centrifuged briefly to remove air bubbles.

The PCR cocktail was prepared according to the following:

| Components | Final Concentration |
| --- | --- |
| 10X PCR Buffer minus Mg (GibcoBRL ®): | 20 mM Tris-HCl (pH 8.4), 50 mM KCl |
| 2 mM dNTPs mixture (GibcoBRL ®): | 0.2 mM each |
| 50 mM MgCl$_2$ (GibcoBRL ®): | 1.3 mM |
| Primers: | |
| 20 μM Casein4 | 0.5 μM |
| 20 μM CaseinDde2 | 0.5 μM |
| Taq DNA Polymerase 5 U/μl (GibcoBRL ®): | 0.75 units per reaction |

The primers used are:

```
                                        (SEQ ID NO: 2)
Casein4      5'-CCTTCTTTCCAGGATGAACTCCAGG-3'

(SEQ ID NO: 1)
CaseinDde2   5'GAGTAAGAGGAGGGATGTTTTGTGGGAGGCTCT-3'
```

PCR was carried out on an MJ Research PTC200 (hot bonnet) using the following protocol:

| 1 cycle | 94.0° C. | 4 min | |
| --- | --- | --- | --- |
| 35 cycles | 94.0° C. | 30 sec | Denature |
| | 60.0° C. | 30 sec | Anneal |
| | 72.0° C. | 30 sec | Extend |

| 1 cycle | 72.0° C. | 4 min |
| --- | --- | --- |
| end | 4.0° C. | |

Following PCR, restriction enzyme cocktail (10 μl) was added and the mixture incubated at 37° C. overnight. The restriction enzyme cocktail was prepared according to the following:

| Components | Final Concentration |
| --- | --- |
| Dde I 10 U/μl (GibcoBRL ®) | 4.5 units per reaction |
| REACT ® 3 (GibcoBRL ®) | 25 mM Tris-HCl (pH 8.0), 5.0 mM MgCl$_2$, 50 mM NaCl |

The amplification product (10 μl) was analysed by electrophoresis (80V, 1 hour) in ethidium bromide stained agarose gel (3%, 1× TBE).

Figure 6:
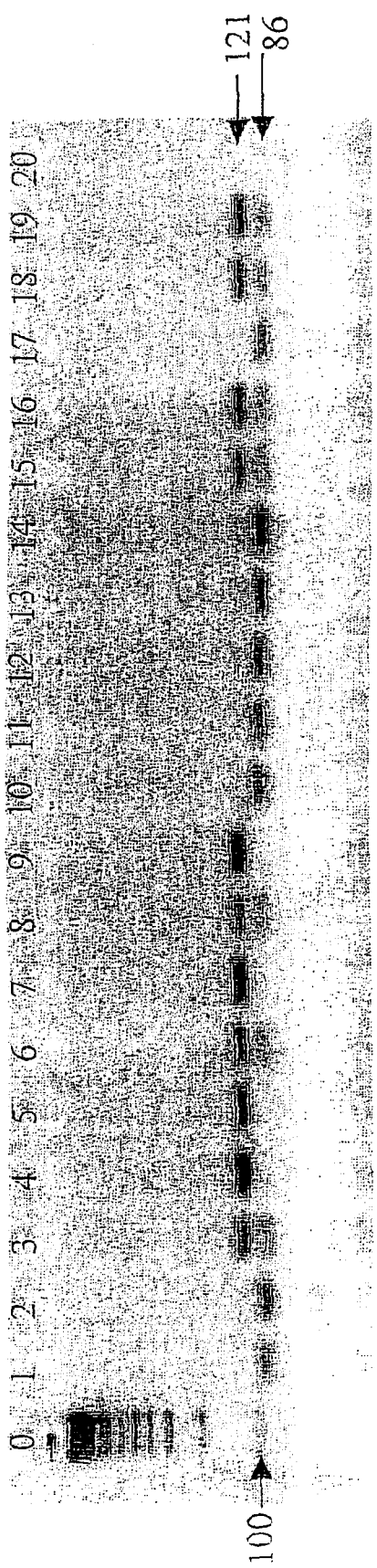
FIG. 6 shows the electrophoresis results for the ACRS genotyping method.

FIG. 6 shows the results of 20 samples analysed by the procedure outlined above.

A size standard ladder was loaded in position 0. The 100 bp band is identified in FIG. 6. The negative control (no DNA) was loaded in position 20. Samples homozygous for CT at positions 2 and 3 of codon 67 of the β-casein gene result in a single 86 bp band when cut by Dde1. This is shown in load positions 1,2,10,11,12,13,14, and 17. Samples not containing CT at positions 2 and 3 of codon 67 of the β-casein gene are not cut by Dde1, leaving a single 121 bp band. This is shown in load positions 4, 5, 7 and 9.

Heterozygous samples result in both cut (86 bp) and uncut (121 bp) bands. This is shown in load positions 3,6,8,15, 16,18 and 19. Because of heteroduplex formation, the uncut band (121 bp) is expected to be more intense than the cut band (86 bp).

Example 2

Primer Extension Method

DNA extracts from hair follicles were prepared using the method described in Example 1. Alternatively, genomicDNA isolated by other methods can be used at a concentration at about 2.5 ng/μl.

A DNA sample (1 μl) from each of 96 animals was placed into a 96 well PCR microtitre plate (or alternatively, from each of 384 animals into a 384 well PCR plate).

For the 96 well plate, a cocktail of the following reagents was prepared in a 1.5 ml microtube. The cocktail (4 μl) was added to each well in the plate with a repeating pipette.

| Reagent | Volume μl |
|---|---|
| Water (HPLC grade) | 222 |
| 10x Hotstar Taq PCR buffer containing 15 mM MgCl₂ | 50 |
| HotStar Taq Polymerase (5 U/μl) | 4 |
| 25 mM MgCl₂ | 20 |
| dNTP 25 mM | 4 |
| Forward and reverse primer mix Forward: actggattatggactcaaagatttg (SEQ ID NO: 7) Reverse: aaggtgcagattttcaacat (SEQ ID NO: 8) (1 μM each primer) | 100 |

PCR was carried out using the following protocol:

| 1 cycle: | 95° C. 15 minutes |
|---|---|
| 45 cycles: | 95° C. 20 seconds |
| | 56° C. 30 seconds |
| | 72° C. 1 minute |
| 1 cycle: | 72° C. 3 minutes |
| end | 4° C. |

The following SAP solution was prepared in a 1.5 ml microtube:

| Reagent | Volume μl |
|---|---|
| Nanopure water | 792.54 |
| hME Buffer (Sequenom, San Deigo) | 88.06 |
| Shrimp alkaline phosphatase | 155.4 |

The solution was mixed well and centrifuged for ten seconds at 5000 RPM.

SAP solution (2 μl) was transferred to each well of the plate containing the samples. The plate was incubated using a thermocycler at 37° C. for 20 minutes, 85° C. for 5 minutes, and then holding at 4° C.

The following extension cocktail was prepared in a 1.5 μl microtube:

| Reagent | Volume μl |
|---|---|
| Nanopure Water | 895.11 μl |
| Sequenom 10x hME extend buffer with 2.25 mM ddA, ddC, ddT, dG | 103.6 μl |
| Primer (100 uM) RMA6 R: gttttgtgggaggctgtta (SEQ ID NO: 9) | 27.97 μl |
| Thermosequenase (32 U/μl) | 9.32 μl |

The extension cocktail (2 μl) was added to each well of the sample plate. The plate was sealed and thermocycled as follows:

| 1 cycle: | 94° C. for 2 minutes |
|---|---|
| 40 cycles: | 94° C. for 5 seconds |
| | 52° C. for 5 seconds |
| | 72° C. for 5 seconds |
| End | 4° C. |

Figure 8:
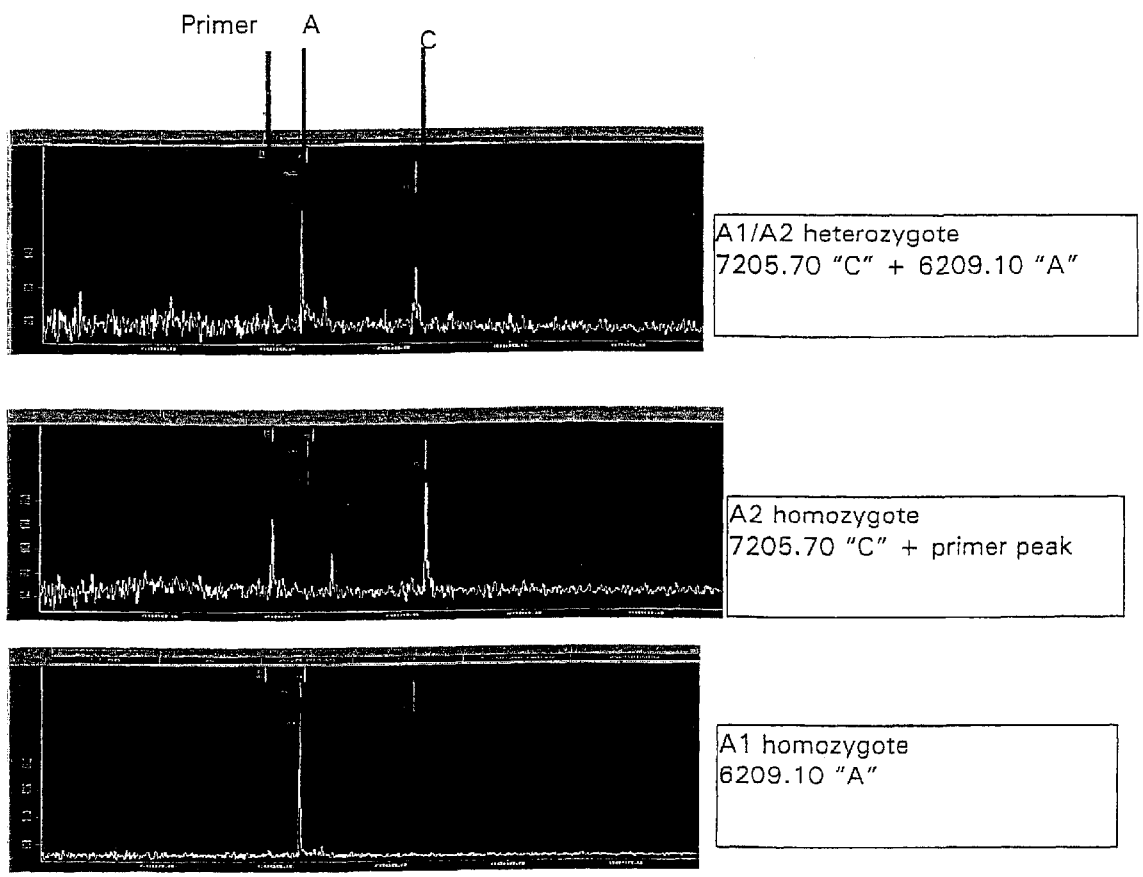
FIG. 8 shows mass spectrometry profile results for the Primer Extension genotyping method.

Prior to mass spectrometry the samples were cleaned using SpectroCLEAN and then analysed using MALDI-TOF MS. The profiles obtained for homozygous and heterozygous animals for the CCT and CAT SNPs are shown in FIG. 8. The location of the primer, analyte A and analyte C extension products are shown.

INDUSTRIAL APPLICATION

The invention provides a useful food product capable of increasing the health of an individual, or the health of a population. The invention relates to a method of preventing or treating coronary heart disease in a human population which derives some of its food intake from milk or other dairy products by reducing or substantially eliminating the presence of β-casein $A^1$ within the diet of that population.

REFERENCES

1. Aleandri, R., Buttazzoni, L. G., Schneider, J. C., Caroli, A., and Davoli, R. (1990) J. Dairy Sci., 73, 241–255.
2. Aschaffenburg, R. (1961) Nature, 192, 431–432.
3. Bassette, R., and Acosta, J. S. (1988) Fundamentals of Dairy Chemistry, $3^{rd}$ Ed.,—Chapter 1: Composition of Milk (Ed. Wong, N. P.) Van Nostrand Reinhold, New York, pp 1–38.
4. Bovenhuis, H., van Arendonk, J. A. M., and Korver, S. (1992) J. Dairy Sci., 75, 2549–2559.
5. Gonyon, D. S., Mather, R. E., Hines, H. C., Haenlein, G. F. W., Arave, C. W., and Gaunt, S. N. (1987) J. Dairy Sci., 70, 2585–2598.
6. Heinecke, J. W. (1999) FASEB J., 13, 1113–1120.
7. Jakob, E. and Puhan, Z. (1997) Bulletin of the IDF, 304, pp 2–3 and 6–8.
8. Jinsmaa, Y. and Yoshikawa, M. (1999) Peptides, 20, 957–962
9. McLean, D. M., Graham, E. R. B., Ponzoni, R. W., and McKenzie, H. A. (1984) J. Dairy Res., 51, 531–546.
10. Ng-Kwai-Hang, K. F., Monardes, H. G., and Hayes, J. E., (1990) J. Dairy Sci., 73, 3414–3420.
11. Peterson, R. F., and Kopfler, F. C. (1966) Biochem. Biophys. Res. Commun., 22, 388–392.
12. Steinberg, D., Parthasarathy, S., Carew, T. E., Khoo, J. C. and Witzum, J. L. (1989) N. Engl. J. Med., 320, 915–924.
13. Torreilles, J. and Guerin, M. C. (1995) French Compt. Rendu Seances Soc. Biol. Filial, 189, 933–945.

What is claimed is:

1. A method of producing milk suitable for use in the treatment or prevention of coronary heart disease from one or more lactating bovines which milk is substantially free of β-casein $A^1$ but which contains any one or more of β-caseins $A^2$, $A^3$, B, C, D and E, the method including the steps of:
   (i) testing DNA or RNA from cells containing DNA or RNA obtained from one or more lactating bovines for the presence of DNA or RNA encoding β-casein $A^1$;
   (ii) selecting bovines which do not have any DNA or RNA encoding for β-casein $A^1$; and
   (iii) milking the selected bovines.

2. A method as claimed in claim 1 wherein the one or more lactating bovines are *Bos taurus* bovines.

3. A method as claimed in claim 1 wherein the milk produced is substantially free of β-casein $A^1$ and the β-casein contained in the milk comprises greater than 95% by weight β-casein $A^2$.

4. A method as claimed in claim 1 wherein the milk produced is substantially free of β-casein $A^1$ and the β-casein contained in the milk comprises approximately 100% by weight β-casein $A^2$.

5. A method of producing milk suitable for use in the treatment or prevention of coronary heart disease from one or more lactating bovines which milk is substantially free of β-caseins $A^1$, B and C but which contains any one or more of β-caseins $A^2$, $A^3$, D and E, the method including the steps of:
   (i) testing DNA or RNA from cells containing DNA or RNA obtained from the one or more lactating bovines for the presence of DNA or RNA encoding any one or more of β-caseins $A^1$, B and C;
   (ii) selecting bovines which do not have any DNA or RNA encoding for any one or more of β-caseins $A^1$, B and C; and
   (iii) milking the selected bovines.

6. A method as claimed in claim 5 wherein the one or more lactating bovines are *Bos taurus* bovines.

7. A method as claimed in claim 5 wherein the milk produced is substantially free of β-casein $A^1$ and the β-casein contained in the milk comprises greater than 95% by weight β-casein $A^2$.

8. A method as claimed in claim 5 wherein the milk produced is substantially free of β-casein $A^1$ and the β-casein contained in the milk comprises approximately 100% by weight β-casein $A^2$.

9. A method of producing milk suitable for use in the treatment or prevention of coronary heart disease from one or more lactating bovines which milk is substantially free of β-casein $A^1$ but which contains β-casein $A^2$, the method including the steps of:
   (i) testing DNA or RNA from cells containing DNA or RNA obtained from the one or more lactating bovines for the presence of DNA or RNA encoding β-casein $A^2$;
   (ii) selecting bovines which are homozygous for DNA or RNA encoding for β-casein $A^2$; and
   (iii) milking the selected bovines.

10. A method as claimed in claim 9 wherein the one or more lactating bovines are *Bos taurus* bovines.

11. A method as claimed in claim 9 wherein the milk produced is substantially free of β-casein $A^1$ and the β-casein contained in the milk comprises greater than 95% by weight β-casein $A^2$.

12. A method as claimed in claim 9 wherein the milk produced is substantially free of β-casein $A^1$ and the β-casein contained in the milk comprises approximately 100% by weight β-casein $A^2$.

13. A method of producing milk suitable for use in the treatment or prevention of coronary heart disease from one or more lactating bovines which milk is substantially free of β-casein $A^1$ but which contains any one or more of β-caseins $A^2$, $A^3$, D and E, the method including the steps of:
   (i) testing DNA or RNA from cells containing DNA or RNA obtained from the one or more lactating bovines for the presence of DNA or RNA encoding any one or more of β-caseins $A^2$, $A^3$, D and E;
   (ii) selecting bovines which have DNA or RNA encoding only for any one or more of β-caseins $A^2$, $A^3$, D and E; and
   (iii) milking the selected bovines.

14. A method as claimed in claim 13 wherein the one or more lactating bovines are *Bos taurus* bovines.

15. A method as claimed in claim 13 wherein the milk produced is substantially free of β-casein $A^1$ and the β-casein contained in the milk comprises greater than 95% by weight β-casein $A^2$.

16. A method as claimed in claim 13 wherein the milk produced is substantially free of β-casein $A^1$ and the β-casein contained in the milk comprises approximately 100% by weight β-casein $A^2$.

17. A method of producing milk suitable for use in the treatment or prevention of coronary heart disease from one or more lactating bovines which milk is substantially free of β-casein $A^1$ but which contains β-casein $A^2$, the method including the steps of:
   (i) testing DNA or RNA from cells containing DNA or RNA obtained from the one or more lactating bovines for the presence of DNA or RNA encoding β-casein $A^1$ and DNA or RNA encoding β-casein $A^2$;

(ii) separating bovines which are homozygous for DNA or RNA encoding β-casein $A^2$ from bovines which either have DNA or RNA encoding β-casein $A^1$ or which have DNA or RNA encoding both β-casein $A^1$ and β-casein $A^2$; and (iii) milking the bovines which are homozygous for DNA or RNA encoding β-casein $A^2$.

18. A method as claimed in claim 17 wherein the one or more lactating bovines are *Bos taurus* bovines.

19. A method as claimed in claim 17 wherein the milk produced is substantially free of β-casein $A^1$ and the β-casein contained in the milk comprises greater than 95% by weight β-casein $A^2$.

20. A method as claimed in claim 17 wherein the milk produced is substantially free of β-casein $A^1$ and the β-casein contained in the milk comprises approximately 100% by weight β-casein $A^2$.

21. A method of producing milk suitable for use in the treatment or prevention of coronary heart disease from one or more lactating bovines which milk is substantially free of β-caseins $A^1$, B and C but which contains any one or more of β-caseins $A^2$, $A^3$, D and E, the method including the steps of:

(i) testing DNA or RNA from cells containing DNA or RNA obtained from the one or more lactating bovines for the presence of DNA or RNA encoding any one or more of β-caseins $A^1$, B and C and DNA or RNA encoding any one or more of β-caseins $A^2$, $A^3$, D and E;

(ii) separating bovines which have any DNA or RNA encoding any one or more of β-caseins $A^1$, B and C from bovines which have DNA or RNA encoding only for any one or more of β-caseins $A^2$, $A^3$, D and E; and (iii) milking the bovines which have DNA or RNA encoding only for any one or more of β-caseins $A^2$, $A^3$, D and E.

22. A method as claimed in claim 21 wherein the one or more lactating bovines are *Bos taurus* bovines.

* * * * *

SEQUENCE LISTING

<160> NUMBER OF SEQ ID NOS: 14

<210> SEQ ID NO 1
<211> LENGTH: 33
<212> TYPE: DNA

```
<213> ORGANISM: Artificial Sequence
<220> FEATURE:
<223> OTHER INFORMATION: Description of Artificial Sequence: Primer

<400> SEQUENCE: 1
gagtaagagg agggatgttt tgtgggaggc tct                                33

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
ccttctttcc aggatgaact ccagg                                         25

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
gttttgtggg aggctgtta                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gttttgtggg aggctgttag                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttttgtggg aggctgttat                                               20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gttttgtggg aggctgttag gga                                           23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer
```

```
<400> SEQUENCE: 7
actggattat ggactcaaag atttg                                         25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
aaggtgcaga ttttcaacat                                               20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
gttttgtggg aggctgtta                                                19

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagtaagagg agggatgttt tgtgggaggc tcttagggat gggccc                  46

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gagtaagagg agggatgttt tgtgggaggc tcttagtgat gggccc                  46

<210> SEQ ID NO 12
<211> LENGTH: 318
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 12
actggattat ggactcaaag atttgttttc cttctttcca ggatgaactc cggataaaat    60 ccacccttt gcccagacac agtctctagt ctatcccttc cctgggccca tccmtaacag   120
cctcccacaa acatccctc ctcttactca aaccctgtg gtggtgccgc ctttccttca    180
gcctgaagta atgggatctc caaagtgaag gaggctatgg ctcctaagca maagaaatg   240 cccttcccta aatatccagt tgagcccttt actgaaagsc agagcctgac tctcactgat   300
gttgaaaatc tgcaccctt                                               318

<210> SEQ ID NO 13
```

```
<211> LENGTH: 56
<212> TYPE: DNA
<213> ORGANISM: Bos sp.

<400> SEQUENCE: 13
cccttgggcc catccctaac agcctcccac aaaacatccc tcctcttact caaacc         56

<210> SEQ ID NO 14
<211> LENGTH: 57
<212> TYPE: DNA
<213> ORGANISM: Bos sp.

<400> SEQUENCE: 14
cccttgggcc catccataac agcctcccac aaaacatccc tcctcttact caaaccc        57
```